US012168031B1

(12) United States Patent
Maraghechi

(10) Patent No.: US 12,168,031 B1
(45) Date of Patent: Dec. 17, 2024

(54) DE-CONSTIPATION METHOD

(71) Applicant: Behrouz Maraghechi, White Plains, NY (US)

(72) Inventor: Behrouz Maraghechi, White Plains, NY (US)

( * ) Notice: Subject to any disclaimer, the term of this patent is extended or adjusted under 35 U.S.C. 154(b) by 0 days.

(21) Appl. No.: 18/410,115

(22) Filed: Jan. 11, 2024

(51) Int. Cl.
| *A61K 36/63* | (2006.01) |
| *A61K 9/00* | (2006.01) |
| *A61K 35/741* | (2015.01) |
| *A61K 36/74* | (2006.01) |
| *A61K 45/06* | (2006.01) |

(52) U.S. Cl.
CPC ............ *A61K 36/63* (2013.01); *A61K 9/0053* (2013.01); *A61K 9/0095* (2013.01); *A61K 35/741* (2013.01); *A61K 36/74* (2013.01); *A61K 45/06* (2013.01)

(58) Field of Classification Search
CPC .... A61K 36/63; A61K 9/0053; A61K 9/0095; A61K 35/741; A61K 36/74; A61K 45/06
See application file for complete search history.

(56) References Cited

U.S. PATENT DOCUMENTS

| 4,476,121 | A | 10/1984 | Moss |
| 5,126,143 | A | 6/1992 | Nakashima et al. |
| 7,238,380 | B2 * | 7/2007 | Stillman ................. A23L 33/21 426/74 |
| 9,693,972 | B2 | 7/2017 | Allio et al. |
| 2004/0175444 | A1 | 9/2004 | Baik et al. |
| 2005/0058671 | A1 | 3/2005 | Bedding et al. |
| 2005/0152989 | A1 | 7/2005 | Pelham et al. |
| 2007/0259059 | A1 | 11/2007 | Eidenberger |
| 2012/0308586 | A1 | 12/2012 | Villarrubia et al. |
| 2014/0212494 | A1 | 7/2014 | Hamaker et al. |
| 2017/0252392 | A1 | 9/2017 | Hwang et al. |
| 2021/0154257 | A1 | 5/2021 | Brown et al. |
| 2022/0241350 | A1 | 8/2022 | Whitlock et al. |

FOREIGN PATENT DOCUMENTS

WO 2008096171 8/2008

OTHER PUBLICATIONS

Bladder & Bowel Community "8 Remedies To Relieve Constipation" Bladder and Bowel Support Company Limited, online <www.bladderandbowel.org/bowel/bowel-treatments/8-remedies-to-relieve-constipation-bladder-bowel-community/>, archived Dec. 7, 2023, 4 pages (Year: 2023).*

* cited by examiner

*Primary Examiner* — Aaron J Kosar
(74) *Attorney, Agent, or Firm* — Goldstein Law Offices, P.C.

(57) ABSTRACT

Methods for treating a patient having constipation, the methods including consuming first, a prescribed daily first diet upon waking from sleep that can include specified: a liquid, an oil, a fruit, a vegetable, a first main meal, or a combination thereof; consuming second, a prescribed daily second diet including a salad, oil, and water; consuming third, a prescribed daily second main meal contemporaneously with consuming the salad, or at least 60 to 90 minutes after consuming the salad; consuming fourth, at least a minimum portion of additional water, after waiting a minimum of 45 minutes from consuming the salad, or after waiting 60 to 90 minutes after a main meal, or both; and then exercising or a sedentary waiting, for a period of time, while consuming additional water.

21 Claims, 2 Drawing Sheets

DE-CONSTIPATION METHOD

CROSS-REFERENCE TO RELATED APPLICATIONS

This application is a nonprovisional utility application and is without a provisional patent application.

TECHNICAL FIELD

The present disclosure relates generally to a de-constipation method. More particularly, the present disclosure relates to a method for treating constipation symptoms.

BACKGROUND

Constipation is a pervasive digestive issue. Its onset can be attributed to a variety of factors, from dietary habits to reduced physical activity, and even certain medications. While there are pharmaceutical solutions available, there is a growing preference for natural, non-invasive remedies.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a method for treating a patient having constipation or a de-constipation method.

The disclosure generally provides methods for treating a patient having constipation, including:
- consuming first, a prescribed daily first diet upon waking from sleep that can include specified: a liquid; an oil; a fruit; a vegetable; a first main meal; or a combination thereof;
- consuming second, a prescribed daily second diet including a salad, oil, and water;
- consuming third, a prescribed daily second main meal contemporaneously with consuming the salad, or at least 60 to 90 minutes after consuming the salad;
- consuming fourth, at least a minimum portion of additional water after waiting a minimum of 45 minutes from consuming the salad, or after waiting 60 to 90 minutes after consuming a main meal, or both, and then
- exercising or a sedentary waiting period, while consuming additional water.

In embodiments, the disclosure provides a first method for treating a patient having constipation, comprising:
- consuming first, olive oil; a high-in-fiber fruit having 2.4 wt % fiber or more, a high-in-fiber vegetable having 2.8 wt % fiber or more, or both; and at least 250 ml of water upon wakening from sleep and prior to ingesting any other food or drink;
- consuming second, a salad including fresh uncooked vegetables with 94 wt % water content or more, and fresh uncooked vegetables with 2.8 wt % fiber or more; olive oil; and at least 250 ml of water;
- consuming third, a main meal, or at least 60 to 90 minutes after consuming the salad consuming the main meal;
- consuming fourth, a minimum of at least 375 ml of water, after waiting a minimum of 45 minutes from consuming the salad, or after waiting 60 to 90 minutes after the main meal, or both, and then
- engaging in a physical activity while consuming at least 500 ml of additional water. See Example 1.

In embodiments, the disclosure provides a second method for treating a patient having constipation, comprising:
- consuming first, olive oil; a high-in-fiber fruit with 2.4 wt % fiber or more, a high-in-fiber vegetable with 2.8 wt % fiber or more, or both; and at least 250 ml of water upon wakening from sleep and prior to ingesting any other food or drink;
- consuming second, a salad including fresh uncooked vegetables having 94 wt % water or more, and fresh uncooked vegetables with 2.8 wt % fiber or more; olive oil; and at least 250 ml of water;
- consuming third, a main meal; and
- consuming fourth, after waiting a minimum of 45 minutes from consuming the salad, or 60 to 90 minutes after consuming the main meal, or both, a minimum of at least 375 ml of water, and then
- accomplishing a sedentary waiting period of from 1 to 2 hours while consuming at least 500 ml of additional water. See Examples 2 and 3 having a sedentary waiting period.

In embodiments, the disclosure provides a third method for treating a patient having constipation, comprising:
- consuming first, at least 250 ml of water, coffee, or both, upon waking from sleep and before consuming a midday main meal (where a "main meal" can include any of or a combination thereof a morning main meal (i.e., breakfast), a mid-day meal (i.e., lunch or dinner), or an evening main meal (i.e., dinner or supper);
- consuming second, a salad including fresh uncooked vegetables with 94 wt % water content or more, and fresh uncooked vegetables with 2.8 wt % fiber or more; olive oil; and at least 250 ml of water;
- consuming third, a main meal contemporaneously with consuming the salad, or at least 60 to 90 minutes after consuming the salad;
- consuming fourth, after waiting a minimum of 45 minutes from consuming the salad, or after waiting 60 to 90 minutes after the main meal, or both, a minimum of at least 375 ml of water, and then
- engaging in a physical activity while consuming at least a minimum portion of additional water, such as at least 500 ml of additional water. See Example 4.

Accordingly, the present disclosure provides a natural and non-invasive method for alleviating constipation.

A problem or disadvantage associated with available solutions proposed to help with constipation such as prunes, water, ingesting more fiber does not actually help with constipation, for example, a patient's constipation induced by medication such as antidepressants, and like compounds and therapies.

A solution to the abovementioned problem or disadvantages is provided in the disclosed methods that can include, for example: natural foodstuff in a natural state, having no processed foods, no additives, no sugars, and no salt. The natural foodstuff can include, for example, plain fruit and salad, with extra virgin olive oil, water, and for example, physical activity preferably walking, and are extremely adaptable to many patients.

The disclosed method integrates potent natural food ingredients, such as olive oil, kiwis, and tomatoes. These natural ingredients, in combination with strategic hydration and dietary shifts, foster a harmonized approach to digestive health.

The present disclosure addresses at least one of the foregoing disadvantages of pharmaceutical treatments and discloses an alternative natural, non-invasive remedy for a constipation condition. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

Figure 1:
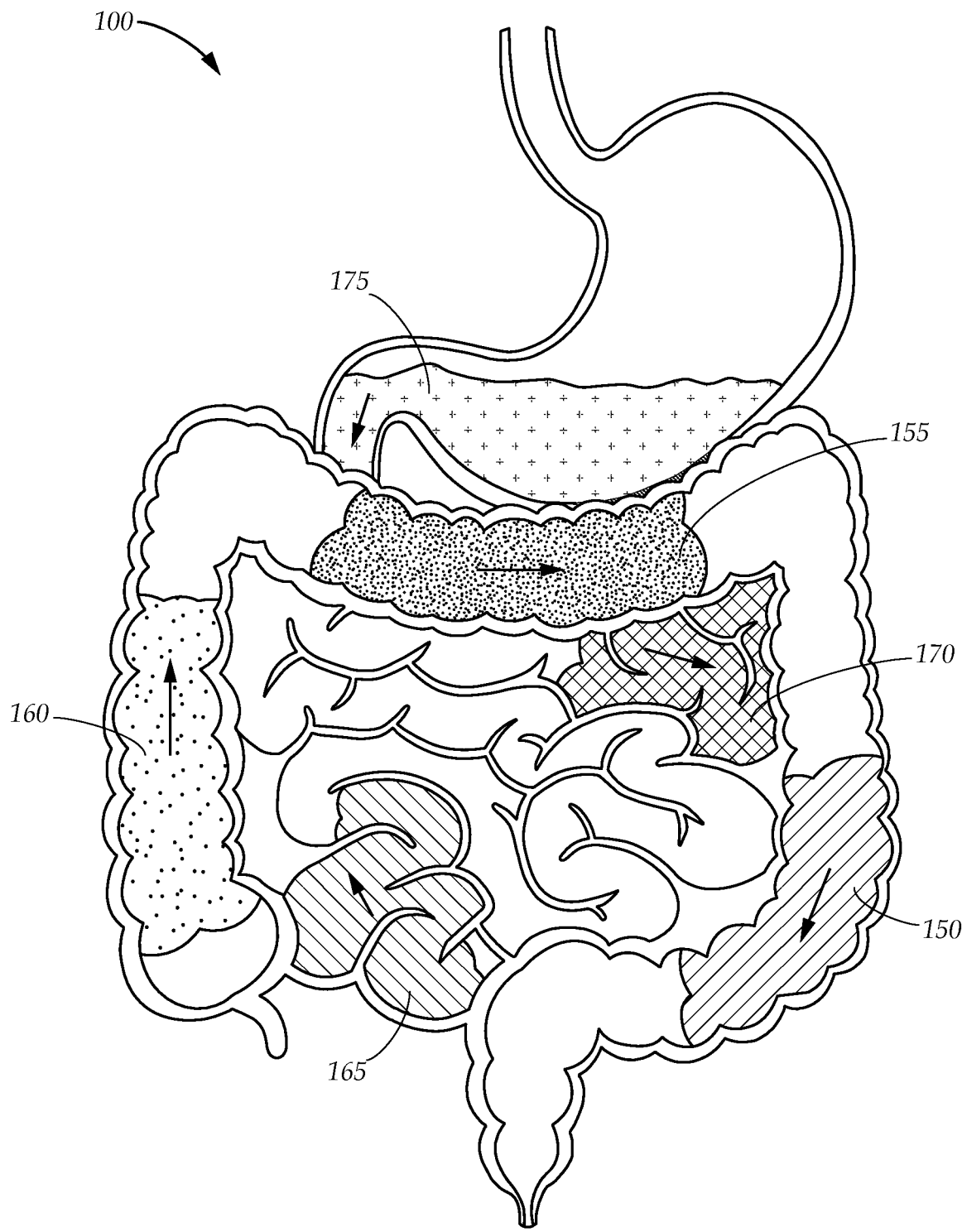
FIG. 1 shows a patient with regular, non-constipated progression where food efficiently moves through the digestive system over a span of three days.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

In embodiments, the disclosure provides a first method for treating a patient having constipation, which is a de-constipation method.

In embodiments, the disclosure provides a first method for treating a patient having constipation, comprising:
consuming first, olive oil; a high-in-fiber fruit having 2.4 wt % fiber or more, a high-in-fiber vegetable having 2.8 wt % fiber or more, or both; and at least 250 ml of water upon wakening from sleep and prior to ingesting any other food or drink;
consuming second, a salad including fresh uncooked vegetables with 94 wt % water content or more, and fresh uncooked vegetables with 2.8 wt % fiber or more; olive oil; and at least 250 ml of water;
consuming third, a main meal or at least 60 to 90 minutes after consuming the salad consuming the main meal;
consuming fourth, after waiting a minimum of 45 minutes from consuming the salad, or after waiting 60 to 90 minutes after the main meal, or both, a minimum of at least 375 ml of water, and then
engaging in a physical activity while consuming at least 500 ml of additional water.

As used herein "main meal" refers to any or all of a breakfast, a brunch, a lunch, a late lunch, an early dinner, a dinner, a late dinner, or supper, but not snacks. In embodiments, a main meal can be purposely excluded, such as a breakfast main meal by foregoing the consuming first, specified diet upon waking from sleep and prior to ingesting any other food or drink.

In embodiments of the disclosed methods, the quantity of specified water portions and foods consumed can be more or less of the specified range depending, for example, upon the capacity or the volume of the patient's gastrointestinal tract, a patient having an extreme body size (e.g., large or small), a patient having a genetic or surgically modified gastrointestinal tract, and like idiosyncrasies.

The method can further comprise consuming, for example, of about 400 to 600 mL, such e.g., 450 to 550 ml, such as 500 mL, of water approximately 30 minutes before each main meal.

The physical activity of the method can include, for example, walking a minimum of 30 minutes, and the walking is continued until a bowel excretion urge is sensed.

The method can further comprise upon waking the patient consumes a cup of regular caffeinated coffee.

The method can further comprise having the patient consuming the salad contemporaneously with plain yogurt.

The disclosed method can be accomplished when all of the steps of the method are completed in about an 8 to 16 hour period.

The disclosed method can be accomplished when the consumed first and second olive oil is about one to four tablespoons, e.g., the first olive oil can be one tablespoon and the second olive oil can be three tablespoons.

The disclosed method can be accomplished if the consumed high-in-fiber fruit is kiwi.

The method can further comprise including a bowel therapy adjuvant in the consumed water.

The disclosed method can be accomplished if the bowel therapy adjuvant is a dietary fiber supplement, e.g., a dietary fiber supplement such as Metamucil®. Here and elsewhere in the present disclosure the dietary fiber supplement-containing product, having psyllium husk as the primary fiber ingredient, is sold under the trademark Metamucil® ("METAMUCIL®").

The disclosed method can be accomplished if the patient is independently being treated with an anti-depression medication, i.e., the patient's constipation condition is exacerbated by an anti-depression medication.

In embodiments, the disclosure provides a second method for treating a patient having constipation, comprising:
consuming first, olive oil; a high-in-fiber fruit with 2.4 wt % fiber or more, a high-in-fiber vegetable with 2.8 wt % fiber or more, or both; and at least 250 mL of water upon wakening from sleep and prior to ingesting any other food or drink;
consuming second, a salad including fresh uncooked vegetables having 94 wt % water or more, and fresh uncooked vegetables with 2.8 wt % fiber or more; olive oil; and at least 250 ml of water;
consuming third, a main meal; and
consuming fourth, after waiting a minimum of 45 minutes from consuming the salad, or 60 to 90 minutes after consuming the main meal, or both, a minimum of at least 375 ml of water, and then accomplishing a sedentary waiting period of from 1 to 2 hours while consuming at least 500 ml of additional water. See Examples 2 & 3 having a sedentary waiting period.

The second method can further comprise consuming of about 400 to 600 mL, e.g. 450 to 550 ml such as 500 mL, of water approximately 30 minutes before each meal.

The second method can further comprise upon waking the patient consumes a cup of regular caffeinated coffee.

The second method can further comprise having the patient consume the salad contemporaneously with plain yogurt.

The disclosed second method can be accomplished if all of the steps of the method are accomplished in about an 8 to 16 hour period.

The disclosed second method can be accomplished if the consumed first and second olive oil dose is about one to four tablespoons total.

The disclosed second method can be accomplished if the consumed high-in-fiber fruit is kiwi.

The second method can further comprise including a bowel therapy adjuvant in the consumed water.

The second method can further comprise having the patient being independently treated with an anti-depression medication, i.e., the patient's constipation condition is exacerbated by anti-depression medication.

The disclosed methods that call for consuming a salad including fresh uncooked vegetables having 94 wt % water or more, can be prepared, for example: at home from fresh ingredients available from a produce vendor or a garden; offered as prepared salad or vegetable mix by a market for take-away; or a restaurant. Fresh uncooked vegetables having 94 wt % water content or more, can be, for example, cucumber, iceberg lettuce, celery, radish, zucchini, tomato, and like vegetables. High-in-fiber fruits can include, for example, apple, pear, kiwi, avocado, passion fruit, strawberry, blueberry, blackberry, raspberry, mango, pomegranate, banana, and like fruits.

In embodiments, the disclosure provides a third method for treating a patient having constipation, comprising:
  consuming first, at least 250 ml of water, coffee, or both, upon waking from sleep and before consuming a main meal, where a main meal can include a morning main meal (i.e., breakfast), a mid-day meal (i.e., lunch or dinner), or an evening main meal (i.e., dinner or supper);
  consuming second, a salad including fresh uncooked vegetables with 94 wt % water content or more, and fresh uncooked vegetables with 2.8 wt % fiber or more; olive oil; and at least 250 ml of water;
  consuming third, a first main meal contemporaneously with consuming the salad, or at least 60 to 90 minutes after consuming the salad;
  consuming fourth, a minimum of at least 375 ml of water, after waiting a minimum of 45 minutes from consuming the salad, or after waiting 60 to 90 minutes after the first main meal or a second main meal, or both the salad and a main meal; and then
  engaging in a physical activity while consuming at least 500 ml of additional water.

Freedom in Dietary Choices: Unlike other methods that enforce restrictive diets, the disclosed de-constipation method places a greater emphasis on specific food components and hydration while allowing individuals the freedom to make personal choices for their main meals like breakfast, lunch, and dinner. This flexibility ensures adherence without sacrificing personal preferences.

Fiber Component: For those individuals or patients grappling with severe constipation, a low or reduced dose of the dietary fiber supplement Metamucil® (i.e., Psyllium husk) can be integrated. Preliminary data indicates that this can notably reduce the need for excessive olive oil, water, and extended walking durations. Specifically, the inclusion of, for example, 5.8 g of Metamucil® (a commercial fiber supplement product) (a third (⅓) of the recommended dose) taken twice daily has shown promising results discussed further in the "Flexibility and Individualization" section below. Incorporating Metamucil® into the disclosed de-constipation method, produced several unexpected results:

Enhanced Synergistic Effect: When a fiber supplement, such as Metamucil® is used in combination with the specific dietary components of the disclosed de-constipation method (such as high-fiber fruits, extra virgin olive oil, strategic hydration, and tailored physical activity), synergistic effects were noticed. This combination appears to enhance the overall efficacy of Metamucil® in alleviating constipation. Patients reported quicker relief and more regular bowel movements compared to using Metamucil® alone.

Reduced Need for Other Laxatives: In the disclosed de-constipation method, the use of Metamucil® at a third of its label recommended dose, combined with the disclosed de-constipation method's other natural components, has been shown to reduce the need for additional laxatives or higher doses of Metamucil®. This is particularly significant for patients who prefer a less medication-intensive approach or for whom excessive laxative use could pose health risks.

Improved Stool Consistency and Comfort: Patients have reported regularity in bowel movements and also improvements in stool consistency, i.e., making passage or the elimination process more comfortable. This is not a commonly emphasized result of standard Metamucil® use and highlights an added benefit of integrating Metamucil® into the disclosed de-constipation method.

Effectiveness in Medication-Induced Constipation: For patients whose constipation is exacerbated by certain medications, such as antidepressants, the incorporation of Metamucil® within the disclosed de-constipation method has shown marked effectiveness. This suggests that the disclosed de-constipation method may have a unique role in addressing medication-induced constipation, where Metamucil® alone might not be as effective.

General Digestive Health Improvement: Beyond just alleviating constipation, the disclosed de-constipation method, inclusive of Metamucil®, appears to contribute to overall digestive health. This could be due to the holistic nature of the disclosed de-constipation method, which can include hydration, diet, and physical activity, together with the fiber supplement.

In conclusion, while Metamucil® is well recognized for its effectiveness in treating constipation, its integration into the disclosed method has produced enhanced and unexpected results.

Stages of the Method: The disclosed de-constipation method consists of strategically structured stages crafted to invigorate the digestive system, regulate bowel movements, and promote detoxification. Depending on the severity of constipation and individual preferences, one may choose to follow 1, 2, 3, or even 4 stages that take place over several days such as two days.

The stages and steps of the disclosed method are exemplified as follows:

Day 1-Stage 1, Morning Routine: Eat two medium-sized kiwis or equivalent high-in-fiber fruits (e.g., having 2.4 wt % fiber or more) before breakfast to promote healthy digestion;

Consume one tablespoon of olive oil to lubricate the digestive system; and optionally, drink a cup of regular caffeinated coffee, known for its stimulant effect on the bowels.

If the Final Stage is not followed by the foregoing Morning Routine, drink one glass of water (e.g., 250 ml).

Day 1-Stage 2, Salad Preparation: Prepare a plate of salad using ingredients such as lotus (i.e., aquatic plant), tomatoes, cucumber, shredded carrot, and avocado. The total weight of these ingredients can be, for example, about 250 g; and add three tablespoons of plain yogurt and up to three tablespoons of extra virgin olive oil for added nutrition and lubrication.

Optionally, a patient or caregiver can include, for example, balsamic vinegar for flavor enhancement in any of the salad ingredients.

If the Final Stage 3 is not followed by the salad consumption, drink one glass (e.g., 250 ml) of water. This glass of water can be taken right after the salad or up to 30 minutes after the salad or after the main meal that might be consumed after the salad.

Day 2-Stage 1, Repeat Morning Routine:

Repeat the morning routine from Stage 1, including the consumption of the olive oil portion and two medium-sized kiwis. Also drink water if necessary, for example, as in Day 1-Stage 2, drink one glass (e.g., 250 ml) of water if the Final Stage is not followed by this additional salad preparation and consumption. This glass of water can be taken right after the salad consumption or up to 30 minutes after the salad consumption or after the main meal that might be consumed after the salad.

Day 2-Stage 2, Repeat Salad Preparation:

Repeat the salad preparation from Day 1-Stage 2, including the selection of ingredients and the addition of yogurt and olive oil. Also drink water if necessary as described in the above Day 2-Stage 1.

Final Stage: Water Consumption and Walking:

The Final Stage should be started after the Morning Routine or salad consumption but before any main meal like breakfast, lunch, or dinner. The Final Stage can also be started, at least, around two hours after any main meals.

Choose the appropriate time to enter the final stage based on constipation severity.

Drink one glass (250 ml) of water to hydrate the body and initiate the cleansing process.

Walk outdoors for 30 to 45 minutes at a comfortable pace, gradually consuming a small bottle (500 ml) of water. The previous glass (250 ml) of water may be taken during the walk instead of before the walk.

Adjust walking duration and water intake based on individual comfort.

Continue walking until the urge to defecate arises, indicating the need for elimination of solid waste.

Initiate walking for a flexible duration, for example, from 15 to 90 minutes, which can be discontinued at the patient's discretion, until the urge to defecate arises. Alternatively, the patient may choose to cease walking and wait for the natural occurrence of waste elimination.

The stages of the method outlined above can be customized and adjusted based on individual needs and responses. It is important to respond to signals and sensation from the body and make necessary modifications while closely monitoring the treatment effects. This personalized approach allows individuals to optimize their digestive health and promote a comprehensive cleansing experience.

Supporting Evidence: The disclosed method is supported by empirical data and aligns with existing scientific knowledge, indicating its effectiveness in addressing constipation and promoting healthy digestion. Key points of supporting evidence include:

1. Empirical Data: Individuals who have implemented this disclosed method have reported significant improvements in reducing constipation symptoms and boosting bowel movement regularity. They experienced increased frequency, ease, and completeness of bowel movements, resulting in relief and improved digestive well-being.

2. Scientific Knowledge: The selection of natural food ingredients in the disclosed de-constipation method is based on their recognized roles in promoting healthy digestion. For example, kiwis are known for their high-in-fiber content (e.g., having 2.4 wt % fiber or more) and natural laxative properties, facilitating smoother passage of stool. Olive oil acts as a lubricant, reducing friction and promoting natural bowel movement. Coffee, a stimulant, enhances intestinal contractions and promotes regular bowel movements. Adequate water intake supports overall digestive health and optimal stool consistency.

3. Flexibility and Individualization: The disclosed method allows for adjustments and variations based on personal preferences and responses, ensuring optimal results for each individual. This individualized approach enhances the effectiveness and adaptability of the disclosed de-constipation method. Patient number 1 aimed to diminish the olive oil in his salad from one tablespoon to none, substituting it with one rounded teaspoon of METAMUCIL® a psyllium fiber supplement containing 3 g of dietary fiber. Although he maintained the intake of one tablespoon of olive oil in the morning, he opted for the fiber supplement in lieu of olive oil in his salad. After dissolving the METAMUCIL® in 250 ml of cold water, he consumed it after the kiwi and olive oil ingestion during his morning routine. Notably, he was under a 50 mg dosage of the Nortriptyline antidepressant. After a two-week adjustment period, he consistently achieved complete bowel movements. This was observed with a water intake of 1000 ml during a 60-minute walk.

4. Observed Outcomes: Individuals following the disclosed de-constipation method have experienced complete expulsion of waste material and regulated bowel movements, further supporting the efficacy of the disclosed de-constipation method. These outcomes, combined with positive feedback, indicate that the disclosed treatment method offers a natural and non-invasive approach to address constipation and promote healthy digestion.

Considerations for Variations: The disclosed de-constipation method allows for customization and adjustments to meet the unique needs and preferences of individuals and address varying levels of constipation severity. Here are some examples of selected considerations for method variations and modifications:

1. Final Stage Selection: Individuals can choose their Final Stage based on the severity of their constipation. For example, those aiming for a regulated bowel movement every other day may start at Day 1-Stage 2 (assuming that a complete bowl movement was on Day 1-Stage 2) and have the Final Stage after Day 3-Stage 1, resulting in a 48-hour interval between bowl movements. The number of stages can be tailored to the severity of constipation, providing flexibility and individualized treatment.

2. Incremental Progression: Gradually progressing through the stages allows individuals to assess their response and make adjustments accordingly. Starting with lower stages and gradually increasing can help find the optimal stage without causing discomfort or disruption of daily routines.
3. Olive Oil Quantity: The amount of olive oil consumed can be adjusted based on individual tolerance and response. Starting with a lower amount and gradually increasing, while monitoring the response, allows for personalized adjustment to achieve the desired effect.
4. Water Intake: The quantity of water consumed during the disclosed method can vary based on individual preferences and needs. Some individuals may require more water to maintain hydration and promote healthy bowel movements, while others may need less. Adequate hydration is crucial for supporting overall digestive health.
5. Additional Ingredients: The disclosed method accommodates the inclusion or substitution of ingredients based on personal preferences and responses. For example, optional consumption of coffee can be omitted or replaced with caffeinated alternatives such as tea, cola, soda, or even additional water. Similarly, salad ingredients can be modified to align with personal taste or dietary restrictions while maintaining the core principles of the disclosed method.

It is important to note that individual patients should closely monitor their response and consider a consult with a healthcare professional, especially if they have underlying health conditions or are taking medications that may interact with certain ingredients. Adapting the disclosed method to individual needs enhances its effectiveness and ensures a personalized approach to address constipation.

Conclusion: By combining natural ingredients, hydration strategies, physical activity, and dietary fibers, when necessary, the disclosed method presents an innovative solution to constipation. With an emphasis on personalization and adaptability, the disclosed method ensures individuals can achieve optimal digestive health.

These additional insights highlight the versatility and adaptability of the routine, making it accessible to a wider range of individuals. By offering alternative methods and acknowledging individual preferences, we can empower more people to find a constipation management approach that suits their specific needs. Publications of interest include, for example:

Hwang, et al. (US 2017/0252392) mention using certain health foods for ameliorating or preventing constipation, see paragraph 0029 therein that specifically mentions a fermented product of cassia seeds.

Baik, et al. (US 2004/0175444) mention use extracts such as tealeaf and radish and like fruits and vegetables as natural food ingredients to prevent or alleviate constipation, see for example, paragraphs 0067 to 0077 therein.

EXAMPLES

Example 1 (Actual) The disclosed method has three main steps that can be completed within 8 to 24 hours. Preferably, the three main steps can be completed within a 12 to 16 hour period or less.

Step 1: Consuming olive oil, for example one tablespoon, high-in-fiber fruits, for example, with 2.4 wt % fiber or more, and vegetables, for example, with 2.8 wt % fiber or more, that is a fruit, a vegetable, or both, for example, a kiwi, and at least 250 mL of water upon wakening from sleep and prior to ingesting any other food or drink. In embodiments, this step 1 can optionally include ingesting an exception drink such as consuming coffee, such as regular or decaffeinated. In essence, Step 1 is accomplished before breakfast, preferably, as soon as the person wakes up and on an empty stomach.

Step 2: Consuming a salad with fresh uncooked vegetables (the vegetables having high water content, for example, of greater than 2.5 wt %) with up to three tablespoons of olive oil and at least 250 ml of water. This glass of water is preferably taken 30 minutes before the salad, or prior to eating a main meal or at least 60 to 90 minutes after eating a main meal. In embodiments, this step 2 can optionally include consuming three tablespoons of plain yogurt for a possible probiotic laxative effect. Note that there is no time restriction between having the salad and having a main meal. In embodiments, the patient may consume the salad and the main meal separately or contemporaneously.

Step 3: After completing step 1, or after step 2 followed by a minimum waiting period of 45 minutes, the patient consumes at least 375 ml of water. Subsequently, the patient engages in a walking activity for a minimum duration of 30 minutes. This walking activity can be performed outdoors, or alternatively, indoors using a treadmill, stepper, indoor track, gymnasium, or similar facilities, especially if outdoor conditions are unfavorable. During the walk, the patient consumes an additional minimum of 500 ml of water. The walking duration is adaptable to the patient's comfort and preference. The patient may choose to continue walking until the urge for bowel excretion is felt or may opt to discontinue walking and wait for the natural occurrence of waste elimination. If the patient experiences a bladder excretion urge, it can be addressed, but the chosen activity (walking) should ideally be resumed until the bowel excretion urge is felt. If the patient is not ambulatory, other activities can include, for example, leg and torso exercise, accomplished in a chair or a bed.

Example 2 (Actual) Example 1 can be accomplished with the following exception. The Step 3 activity (i.e., walk) can be omitted and instead the patient accomplishes the specified water portion consumption, for example, in from 15 to 30 minutes, and then accomplishes a sedentary waiting period of, for example, from 1 to 2 hours.

Example 3 (Actual) Example 1 or Example 2 can be accomplished with the following exception. The enumerated steps of Example 1 or Example 2 are accomplished and additionally include administering a known bowel therapy adjuvant, an as-yet unknown bowel therapy adjuvant, or like bowel therapy adjuvant, for treating constipation. The Step 3 activity (i.e., walk) can be accomplished or omitted and instead the patient accomplishes the specified water portion consumption, for example, in from 15 to 30 minutes, and then accomplishes a sedentary waiting period of, for example, from 1 to 2 hours. Omitting the activity component may necessitate a slight adjustment, either by extending the waiting period before a bowel movement or by marginally increasing water consumption during the final stage to achieve the desired effect. Known bowel therapy adjuvants for treating constipation can include, for example, the aforementioned Metamucil®.

Other bowel therapy adjuvants can include, for example: Fiber Supplements: psyllium husk (as in METAMUCIL®), methylcellulose (e.g., CITRUCEL®), polycarbophil (e.g., FIBERCON®), and wheat dextrin (e.g., BENEFIBER®); Stool Softeners: docusate sodium (e.g., COLACE®), and docusate calcium; Osmotic Laxatives: polyethylene glycol (e.g., MIRALAX®), lactulose, and magnesium hydroxide (e.g., MILK OF MAGNESIA®); Stimulant Laxatives: Senna (e.g., seneket SENOKOT®), and bisacodyl (e.g., DULCOLAX®); Lubricant Laxatives: mineral oil; Natural and Herbal Remedies: aloe vera, cascara sagrada, slippery elm, and rhubarb; Probiotics: lactobacillus strains, and bifidobacterium strains; Prebiotics: inulin, and fructooligosaccharides.

The specific choice of adjuvants may depend on the individual's specific needs, tolerances, and the disclosed method's overall framework. It's also important to note that while some of these adjuvants are available over the counter, others might require a prescription or should be used under medical supervision, especially for individuals with specific health conditions or those on certain medications. The selection of an appropriate adjuvant should be based on the individual's health status and the specific objectives of the method.

A main aspect of the disclosed method seeks to alleviate constipation symptoms without resorting to medication. The main aspect emphasizes the importance of natural food ingredients, hydration techniques, physical activity, and in instances of more severe constipation, the inclusion of a dietary fiber supplement.

Kiwi and Salad: In the disclosed method, two kiwis used in Stage 1, would weigh around 190 g in total. A typical salad, in Stage 2, may be composed of the following items: lettuce, 60 g; carrot, 40 g; cucumber, 60 g; avocado, 50 g; and tomato, 50 g, for a total of 260 g.

General Data on Bowel Movement Induction Method

Following a specific sequence, the individual number 1 observed bowel movement patterns by adjusting variables such as olive oil consumption, water intake, and walk duration.

The disclosed methods can include a structured series of stages over consecutive days, culminating in a Final Stage. The Table 1 summarizes the results of these observations for the enumerated patients (1 to 22): The number of tablespoons (tblsp) of olive oil is what has been used in daily salad by the patient; water intake is the volume of water taken during the walk by the patient; V 150 represents the antidepressant Venlafaxine at 150 mg; and N 50 represents the antidepressant Nortriptyline at 50 mg.

TABLE 1

|    | Month-Date | Olive oil (tblsp) | Water Intake (ml) | Walk time (mins) | Medication (mg) | Waittime between coffee and walk (mins) | Bowel Movement | Note # |
|----|------------|-------------------|-------------------|------------------|-----------------|------------------------------------------|----------------|--------|
| 1  | 6-29       | 3                 | 800               | 15               | V15O            | 0                                        | Complete       |        |
| 2  | 7-1        | 3                 | 700               | 25               | V15O            | 0                                        | Complete       |        |
| 3  | 7-3        | 2                 | 1100              | 45               | V15O            | 0                                        | Complete       |        |
| 4  | 7-9        | 2                 | 900               | 45               | V150            | 0                                        | Complete       |        |
| 5  | 7-17       | 2                 | 800               | 35               | V 75 + N 10     | 20                                       | Complete       |        |
| 6  | 7-19       | 2                 | 850               | 0                | V 75 + N 10     | 30                                       | Complete       | 1      |
| 7  | 7-21       | 2                 | 1250              | 60               | V 75 + N 20     | 0                                        | Partial        | 2      |
| 8  | 7-23       | 2                 | 750               | 40               | V 75 + N 20     | 0                                        | Complete       |        |
| 9  | 7-25       | 2                 | 750               | 80               | V 75 + N 20     | 0                                        | Partial        |        |
| 10 | 7-27       | 2                 | 1300              | 70               | V 75 + N 20     | 0                                        | Partial        |        |
| 11 | 7-28       | 2                 | 1450              | 90               | V 75 + N 30     | 0                                        | Partial        | 3      |
| 12 | 7-30       | 3                 | 1450              | 75               | V 75 + N 30     | 0                                        | Complete       |        |
| 13 | 8-6        | 3                 | 950               | 30               | V 75 + N 40     | 0                                        | Complete       | 4      |
| 14 | 8-10       | 2                 | 800               | 40               | N 50            | 0                                        | Complete       | 5      |
| 15 | 8-12       | 2                 | 1350              | 75               | N 50            | 0                                        | Complete       | 6      |
| 16 | 8-26       | 1                 | 1000              | 60               | N 50            | 0                                        | Partial        | 7      |
| 17 | 8-27       | 1                 | 1000              | 30               | N 50            | 0                                        | Complete       | 8      |
| 18 | 8-29       | 1                 | 1000              | 60               | N 50            | 0                                        | Partial        | 9      |
| 19 | 8-30       | 1                 | 1000              | 30               | N 50            | 0                                        | Complete       | 10     |
| 20 | 8-31       | 1                 | 1000              | 60               | N 50            | 0                                        | None           | 11     |
| 21 | 9-1        | 1                 | 880               | 45               | N 50            | 0                                        | Complete       |        |
| 22 | 9-3        | 1                 | 1000              | 50               | N 50            | 0                                        | Complete       |        |

Key Observations and Notes: After several trials and adjustments, the patient was able to tailor the routine according to personal preferences. Notable changes include a reduction of olive oil consumption to two tablespoons per day and an average water intake of around 900 ml during the 45 minute walk.

Note 1: The expected Final Stage, which should have occurred after Day 3-Stage 1, was missed. This resulted in bloating and a partial bowel movement later in the afternoon. The Final Stage was then conducted after Day 3-Stage 2.

Note 2: One stage, specifically Day 2-Stage 2, was missed.

Note 3: The bowel movement was considerable, but not complete (i.e., "partial").

Note 4 and 5: On both these occasions, Day 2-Stage 2 was missed, but bowel movement was complete.

Note 6: The individual patient observed the importance of drinking water during the walk, concluding that walking alone wasn't sufficient to induce a bowel movement.

Notes 7 and 9: These days resulted in a soft stool with a volume equating to approximately ⅓ of a complete bowel movement (i.e., "partial").

Notes 8 and 10: Observing the partial bowel movement from the previous day, the stages were adjusted starting with Day 1-Stage 2 and ending at Day 2-Stage 1. These days replicate the patterns observed in Notes 7 and 9.

Note 11: The patient felt an urge but couldn't achieve a bowel movement for several hours (i.e., "none"). When bowel movement did occur, the movement was partial and required significant effort. The varied consistency of the stool indicated an incomplete bowel movement from the previous day. This observation suggests that attempting a daily bowel movement may not be optimal for this patient without adjustments to olive oil intake, water consumption during walking, or extended walk duration.

By systematically observing and adjusting the variables in the disclosed de-constipation method, if desired individuals can tailor the de-constipation method to their needs, ensuring optimal bowel movement outcomes.

The following section organizes the information and observations in a coherent and understandable manner. Adjustments can be made based on further observations or specific requirements.

Empirical Analysis of Bowel Movement Induction Data

1. Correlation between Water Intake and Walking Duration: A comparison between row #1 and row #2 of Table 1 shows an inverse relationship between water intake and walking time. For a lower water intake (700 mL in row #2), a longer walking duration (25 mins) is required compared to a higher water intake (800 mL in row #1) which needs only 15 min of walking. This implies that water intake can potentially reduce the necessary amount of physical activity for inducing a bowel movement.

2. Effect of Delayed Walking Start: Observations from rows #5 and #6 of Table 1 highlight an intriguing property: delaying the start of walking can reduce its necessary duration. This offers flexibility, especially for those who might find longer durations of walking challenging or inconvenient. Row #6 is particularly intriguing. Despite no walking at all, a bowel movement still occurs, albeit with a delay. This suggests that the preparatory stages create an environment conducive to bowel movements even without the aid of physical activity.

3. Impact of Antidepressants on Constipation: Both Venlafaxine ("V") and Nortriptyline ("N") are known to have constipation as a significant side effect. From the data provided, it's evident that Venlafaxine exacerbated constipation more severely than Nortriptyline. When a patient was receiving the maximum dose of Venlafaxine (150 mg), there was a need for a higher intake of olive oil (at least 2 tablespoons) to combat the constipation. However, when transitioning to Nortriptyline (50 mg), the requirement reduced to just 1 tablespoon, suggesting Nortriptyline's comparatively milder constipating effect.

4. Significance of Preparatory Stages: The initial stages, involving hydration, laxative intake (like olive oil), and fibrous food, seem significant in preparing the digestive system for the final act of bowel movement. The routine appears to have a cumulative effect, where each stage contributes to the end result. As seen in row #6, even without the walking phase, the prior stages sufficiently prepare the system for a bowel movement, given adequate water intake in the final stage.

6. Stool Consistency as an Indicator: Soft stool consistency across the board, irrespective of variations in routine, suggests that the initial stages play a significant role in maintaining optimal hydration levels in the bowel. It further implies a faster transit time and a well-hydrated digestive tract, are essential for easing constipation.

7. Coffee's Accelerative Role: The consumption of coffee before walking suggests at coffee's role in enhancing the bowel movement activity. Caffeine in coffee is known to increase motility in the colon. When combined with walking physical activity, the caffeine and the physical activity can work synergistically.

Conclusions: There is a clear correlation between water intake and the required duration of walking to induce a bowel movement. Increasing hydration can potentially reduce the need for prolonged physical activity. A structured routine, comprising hydration, laxatives, and fibrous food, can produce a conducive environment for bowel movements, even in the absence of physical activity. Delaying the onset of walking can offer flexibility in terms of reduced walking duration while still achieving the desired outcome. Coffee can be a strategic addition to amplify the effects of the routine, especially before physical activity. The use of antidepressants, specifically Venlafaxine and Nortriptyline, has observable impacts on constipation severity and the required mitigation measures, such as olive oil intake.

Recommendations: For individuals wanting to minimize walking duration, increasing water intake or strategically delaying the walking start can be beneficial. Regular monitoring of stool consistency can provide insights into the digestive system's hydration levels and the routine's effectiveness. Monitoring the impact of any medications on bowel movement patterns can provide better insight into personalized routine adjustments. Any alterations to the routine should be done methodically, observing the subsequent effects on bowel movements to understand the interplay between different stages. The analysis aims to dissect the data methodically and highlight the patterns and relationships evident from the observations, providing a foundation for informed decisions and further refinements.

Positive responses from three additional patients: Three additional patients have tested this routine and achieved favorable outcomes. Patient number 2 began his morning on an empty stomach then consumed one tablespoon of olive oil, followed by a large apple. He then drank a cup of coffee accompanied by 250 ml of water. After hydrating with an additional 500 ml of water during a 40-minute walk, he experienced a bowel movement that resulted in complete evacuation. Patient number 3 followed a similar routine, but with a variation: he engaged in a brisk 30-minute walk.

Approximately 60 minutes after concluding his walk, he too experienced a similar complete bowel movement.

Patient number 4, who generally experienced regular morning bowel movements, encountered temporary irregularities. In response, she implemented a modified version of the disclosed de-constipation method, primarily emphasizing hydration and caffeine consumption, without the consumption of between 400 to 800 ml of water on an empty stomach immediately upon waking, followed by consumption of 400 ml of coffee. This streamlined approach effectively and promptly restored her bowel regularity, demonstrating the adaptability and efficacy of a modified method even for those not suffering from chronic constipation. This modified example exemplifies how the disclosed method can be tailored to accommodate varying degrees of constipation severity and individual lifestyle patterns, emphasizing the disclosed method's flexibility in promoting digestive health and regular bowel movements.

Integration of Fiber Supplements: Until now, the approach to managing severe and chronic constipation has been rooted in the use of natural foods in their unprocessed forms. However, by incorporating food-based fiber supplements into the disclosed method, there are several benefits, for example:

Flexibility: One can easily adjust variables like the quantity of olive oil, water intake amount during the walk, and walking duration.

Practicality: Some severe constipation scenarios might necessitate intake of large and potentially inconvenient quantities of certain foods or liquids. In such situations, fiber supplements can act as a balancing agent, potentially decreasing the required intake of other components.

For instance, Individual number 1 (i.e., patient #1) aimed to diminish the olive oil in his salad from one tablespoon to none, substituting it with one rounded teaspoon of Metamucil®—a psyllium fiber supplement containing 3 g of dietary fiber. Although he maintained the intake of one tablespoon of olive oil in the morning, he opted for the fiber supplement in lieu of olive oil in his salad. After dissolving the Metamucil® in 250 ml of cold water, he consumed it post-kiwi and olive oil ingestion during his morning routine. Notably, he had a 50 mg dosage of the Nortriptyline antidepressant. After a two-week adjustment period, he consistently achieved complete bowel movements. This was observed with a water intake of 1000 ml during a 60-minute walk.

Preparatory Stages and the Physics of Bowel Movement: The human digestive system, though complex, follows certain predictable patterns. Depending on various factors like hydration, diet, and even emotional stress, the excretion process can either function smoothly or face challenges. The dynamics and the science of the bowel movement process are discussed below.

Anatomy of the Digestive Tract: A human digestive tract, from ingestion to excretion, includes the mouth, esophagus, stomach, small intestine, large intestine (colon), rectum, and anus. Referring to the Figures, FIG. 1 depicts a regular, non-constipated progression where food efficiently moves through the digestive system over a span of three days. In contrast, FIG. 2 demonstrates slowed transit, characteristic of constipation, where food from Day 1 lags behind in the digestive system. These models, while generalized, derive from both a physiological understanding and observed patterns.

Nature of Stool in Constipation: In those patients not undergoing preparatory stages, stools become hard, dense, and dry. This is due to the prolonged time stool spends in the large intestine, where more water is absorbed by the body, and making the stool harder. Dry stools encounter more friction within the colon, akin to a dry sponge sliding on a surface. This resistance impedes stool/fecal movement, leading to sluggish or "stuck" stool. As time progresses, this stool becomes even drier due to continued water absorption, worsening the issue.

Revolutionizing with the Preparatory Stages:

Hydration: An integral part of the disclosed method, daily hydration of at least eight glasses insures the stool retains water, reducing its dryness and the resultant friction. A moister stool can move freely, promoting smoother motion through the colon.

Natural Laxative-Olive Oil: Acting as an internal lubricant, olive oil makes the stool softer and less resistant to movement. It's akin to adding oil to machinery, ensuring its smooth operation. Moreover, fibrous foods like kiwi and salad bulk up the stool, ensuring it retains water and remains soft.

Enhancing Gravity's Pull: A well-hydrated stool is not just softer but denser and heavier. This increased weight amplifies the effect of gravity, aiding its downward movement for evacuation.

Addition of Fiber: Foods such as kiwi and salad add volume, ensuring a bulkier and softer stool, while the layering effect ensures a uniform distribution of helpful agents throughout the stool, simulating the conditions in non-constipated individuals.

Coffee's Contribution: Including caffeine-rich coffee can also be beneficial, given its known stimulant effects on the colon, enhancing the bowel movement process.

Conclusion: Addressing constipation effectively requires an understanding of its physical dynamics. The preparatory stages, rooted in hydration, diet, and physical activity, work synergistically to combat constipation, ensuring more natural and frequent bowel movements. By incorporating the preparatory stages, individuals can counteract the challenges posed by constipation, promoting a healthier, more efficient digestive process.

FIG. 1 illustrates a non-constipated digestive system. The purpose of FIG. 1 visualizes the progression of food through the digestive system from the morning of Day 1 (not shown) to the morning of Day 3 in a non-constipated individual including: GI tract 100; Day 1's lunch 150; Day 1's dinner 155; Day 2's breakfast 160; Day 2's lunch 165; Day 2's dinner 170; and Day 3's early morning food 175 in the stomach. The GI or digestive tract 100 anatomical components and locations include: mouth; esophagus; stomach; small intestine (consisting of duodenum, jejunum, ileum); large intestine (ascending colon, transverse colon, descending colon, sigmoid colon); rectum; and anus, are readily evident to one of ordinary skill in the art.

Food Distribution in a Non-Constipated Digestive System (FIG. 1)

Day 1's food: breakfast: Likely passed out as stool; lunch: in the descending colon and sigmoid colon; and dinner: in the transverse colon.

Day 2's food: breakfast: in the ascending colon; lunch: in late parts of the small intestine (ileum); and dinner: in the small intestine (likely jejunum).

Day 3's early morning intake (kiwi, olive oil, and coffee): mostly in the stomach and beginning to enter the duodenum.

In FIG. 1 different shades are used to indicate different days' food ration. The directional arrows along the digestive tract show the direction of food movement.

Figure 2:
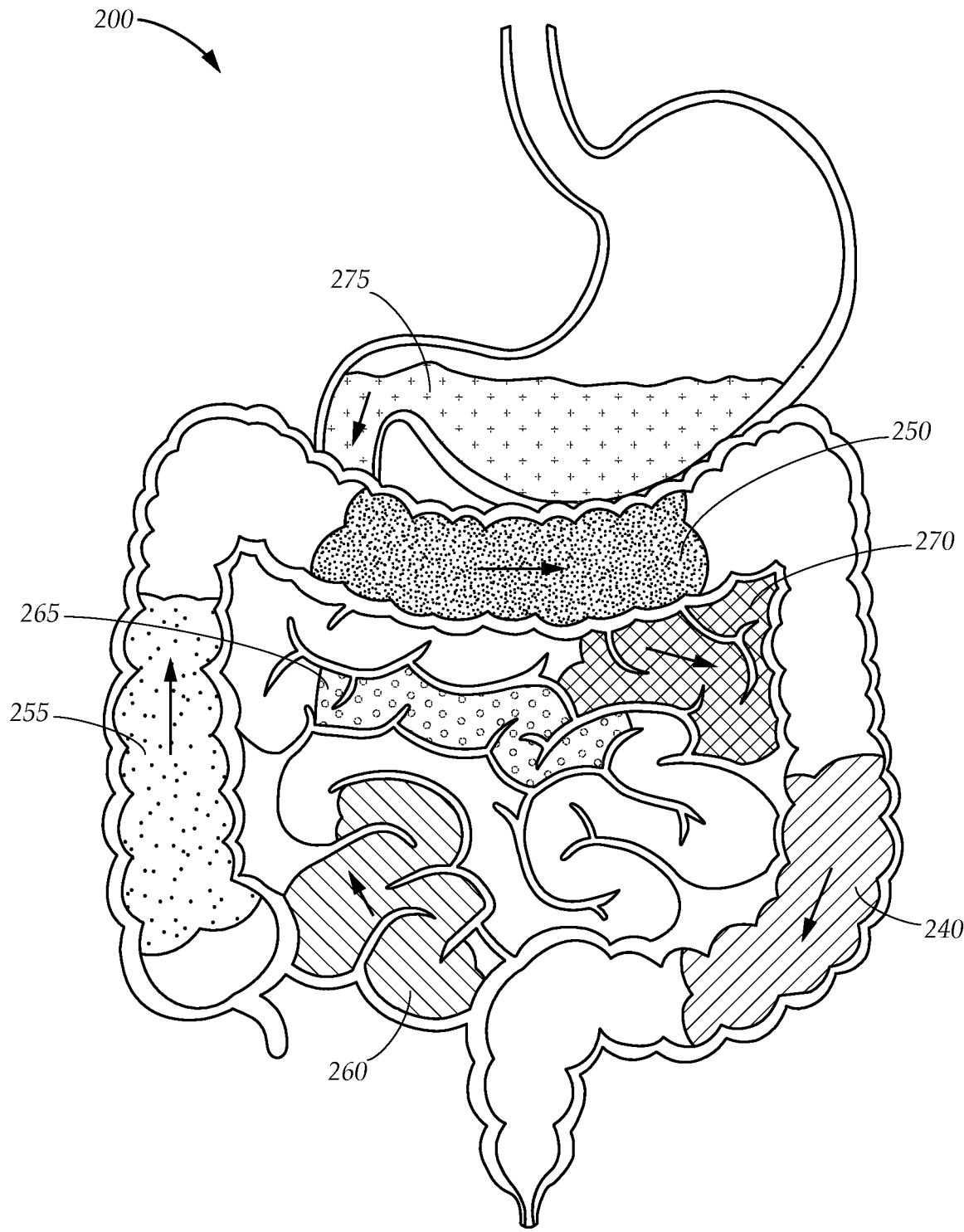
FIG. 2 demonstrates slowed transit, characteristic of constipation, where food from Day 1 lags behind in the digestive system (i.e., extended retention).

FIG. 2 illustrates a constipated digestive system. The purpose of FIG. 2 visualizes the slower progression of food through the digestive system from the morning of Day 1 to the morning of Day 3 in an exemplary constipated individual. Digestive tract components in FIG. 2 are identical to those mentioned and illustrated for FIG. 1.

Food Distribution in a Constipated Digestive System (FIG. 2)

Day 1's food: breakfast: in the descending colon, lunch: positioned in the transverse colon, dinner: might be in the ascending colon.

Day 2's food: breakfast: in the small intestine, primarily in the ileum, lunch: in the middle of the small intestine, dinner: in the earlier portions of the small intestine, such as the jejunum.

Day 3's early morning intake (kiwi, olive oil, and coffee): predominantly in the stomach and beginning to enter the duodenum.

In FIG. 2 different shades are used to indicate different days' food ration in a constipated individual's GI tract 200. The purpose of FIG. 2 visualizes the progression of food through the digestive system from the morning of Day 1's breakfast to the early morning of Day 3 in a constipated individual. The annotations and labels differentiate a constipated individual's passage from a non-constipated individual's passage. Similar to the FIG. 1, FIG. 2 emphasizes the movement and digestion process with the difference that the patient has constipation, including: GI tract 200; Day 1's breakfast 240; Day 1's lunch 250; Day 1's dinner 255; Day 2's breakfast 260; Day 2's lunch 265; Day 2's dinner 270; and Day 3's early morning food 275.

Final Stage: Hydration-Induced Bowel Movement and Gastrointestinal Signaling

In the concluding phase to combat constipation and enhance bowel movement efficiency, there is a focus on the pivotal interaction between the stomach—receiving a substantial volume of water, and the subsequent response of the colon. This stage is integral as it utilizes the gastrocolic reflex, peristalsis, and mass movements to facilitate the digestive process in a natural and non-invasive manner.

Method Integration:

Initial Hydration: The patient starts by consuming a standardized volume of water, such as around 250 ml, to initiate the hydration process. This act is intended to gently stimulate the gastrocolic reflex, which in turn may prompt the colon to prepare for a bowel movement.

Physical Activity Coupled with Hydration: Following this, a 30 to 45-minute walk is encouraged, wherein the individual continues to hydrate with an additional 500 ml of water. This combined approach of physical activity and hydration magnifies the natural peristaltic and mass movement actions of the colon.

Stimulation of Digestive Movements: The walking, although not mandatory for the disclosed de-constipation method to be effective, aids in enhancing the peristalsis, essential for guiding the contents towards the rectum, and mass movements, which efficiently transport larger volumes of waste through the large intestine.

Observation of Body Response: Walking duration and water intake may be tailored based on the individual's response and comfort level. It's noted that modifying the walking component slightly adjusts the timing and efficacy of the bowel movement response.

Physiological Response and Successful Conclusion: Within an hour from the initiation of this stage, the individual is likely to feel the urge to defecate, signaling a successful induction of the natural waste elimination process.

Physiological Explanation:

Gastrocolic Reflex: The introduction of water into the stomach activates the gastrocolic reflex, which in turn accelerates peristalsis throughout the colon.

Peristalsis: Ingested water, when absorbed into the small intestine, enhances its volume and contributes to stool softening. This facilitates its progression towards the rectum. As the ingested water transits through the small intestine, it marginally increases the fluid content at the terminal ileum, which then proceeds into the colon, aiding in moisture transfer to the stool.

Mass Movements: Consistent hydration during the final stage promotes mass movements. These significant, coordinated contractions are crucial for propelling the softened stool in bulk towards the rectum, prompting the urge to defecate.

Conclusion: The Final Stage, "Hydration-Induced Bowel Movement and Gastrointestinal Signaling," marks the culmination of a comprehensive, lifestyle-centric approach to managing constipation. It demonstrates the practical application of physiological knowledge (i.e., the gastrocolic reflex, peristalsis, and mass movements) in a method that is non-pharmacological and harmonizes with the body's intrinsic rhythms. This disclosed de-constipation method offers immediate relief from constipation but can also serve as a preventative measure, promoting long-term gastrointestinal health and regularity.

Example 4 (Actual) Strategic Timing of Water Intake

Examples 1, 2, or 3, can be accomplished with the following exception. The enumerated steps of Examples 1, 2, or 3, are accomplished and additionally include: the patient consumes, for example, 400 to 600 mL, such as about 500 mL, of water approximately 30 minutes before each and every main meal. This additional "pre-hydration" step has a profound impact on bowel movements. This timing of water intake is believed to induce more effective peristaltic waves (i.e., peristaltic resonance).

Example embodiments are described herein with reference to images that are schematic illustrations of idealized embodiments.

In conclusion, herein is presented methods for treating constipation. The disclosure is illustrated by example in the drawing figures, and throughout the written description. It should be understood that numerous variations are possible, while adhering to the inventive concept. Such variations are contemplated as being a part of the present disclosure.

What is claimed is:

1. A method for treating a patient having constipation, comprising in therapeutically effective amounts therefor:
   (i) consuming first, olive oil; a high-in-fiber fruit having 2.4 wt % fiber or more, a high-in-fiber vegetable having 2.8 wt % fiber or more, or both; and at least 250 ml of water, upon wakening from sleep and prior to ingesting any other food or drink;
   (ii) consuming second, a salad including fresh uncooked vegetables having 94 wt % water content or more, and fresh uncooked vegetables with 2.8 wt % fiber or more; olive oil; and at least 250 ml of water;
   (iii) consuming third, a main meal, wherein the main meal is optionally consumed at least 60 to 90 minutes after consuming the salad;
   (iv) consuming fourth, after waiting a minimum of 45 minutes from consuming the salad and/or after 60 to 90 minutes after consuming the main meal, a minimum of at least 375 ml of water, and
   (v) engaging in a physical activity while consuming at least 500 ml of additional water, wherein the process therapeutically effects in the patient a complete bowel movement, daily bowel movements, increased regular bowel movements, and/or improved stool consistency; and wherein said therapeutic effects are greater than the effects in a patient not treated thereby and/or, when further threating with a dietary fiber bowel therapy adjuvant, provides said therapeutic effects greater than treating with the dietary fiber bowel therapy alone.

2. The method of claim 1, further comprising consuming of about 400 to 600 ml of water approximately 30 minutes before each main meal.

3. The method of claim 1, wherein the physical activity includes: walking a minimum of 30 minutes, and the walking is continued until a bowel excretion urge is sensed.

4. The method of claim 1, further comprising upon waking the patient consumes an 8 oz cup of regular caffeinated coffee.

5. The method of claim 1, further comprising the patient consumes the salad contemporaneously with plain yogurt.

6. The method of claim 1, wherein all of the steps of the method are accomplished in about an 8 to 16 hour period.

7. The method of claim 1, wherein the consumed first and second olive oil is about one to four tablespoons.

8. The method of claim 1, wherein the consumed high-in-fiber fruit is kiwi.

9. The method of claim 1, further comprising a bowel therapy adjuvant in the consumed water.

10. The method of claim 9, wherein the bowel therapy adjuvant is a dietary fiber supplement.

11. The method of claim 1, wherein the patient is independently being treated with an anti-depression medication.

12. A method for treating a patient having constipation, comprising in therapeutically effective amounts therefor:
(i) consuming first, olive oil; a high-in-fiber fruit with 2.4 wt % fiber or more, a high-in-fiber vegetable with 2.8 wt % fiber or more, or both; and at least 250 ml of water upon wakening from sleep and prior to ingesting any other food or drink;
(ii) consuming second, a salad including fresh uncooked vegetables having 94 wt % water or more, and fresh uncooked vegetables with 2.8 wt % fiber or more; olive oil; and at least 250 ml of water;
(iii) consuming third, a main meal;
(iv) consuming fourth, after waiting a minimum of 45 minutes from consuming the salad and/or 60 to 90 minutes after consuming the main meal, a minimum of at least 375 ml of water; and
(v) accomplishing a sedentary waiting period of from 1 to 2 hours while consuming at least 500 ml of additional water,
wherein the process therapeutically effects in the patient a complete bowel movement, daily bowel movements, increased regular bowel movements, and/or improved stool consistency; and wherein said therapeutic effects are greater than the effects in a patient not treated thereby and/or, when further threating with a dietary fiber bowel therapy adjuvant, provides said therapeutic effects greater than treating with the dietary fiber bowel therapy alone.

13. The method of claim 12, further comprising consuming of about 400 to 600 ml of water approximately 30 minutes before each meal.

14. The method of claim 12, further comprising upon wakening the patient consumes an 8 oz cup of regular caffeinated coffee.

15. The method of claim 12, further comprising the patient consumes the salad contemporaneously with plain yogurt.

16. The method of claim 12, wherein all of the steps of the method are accomplished in about an 8 to 16 hour period.

17. The method of claim 12, wherein the consumed first and second olive oil is about one to four tablespoons.

18. The method of claim 12, wherein the consumed high-in-fiber fruit is kiwi.

19. The method of claim 12, further comprising including a bowel therapy adjuvant in the consumed water, wherein the adjuvant is optionally a psyllium husk containing dietary fiber supplement.

20. The method of claim 12, wherein the patient is independently being treated with an anti-depression medication.

21. A method for treating a patient having constipation, comprising in therapeutically effective amounts therefor:
(i) consuming first, at least 250 ml of water, coffee, or both, upon waking from sleep and before consuming a main meal;
(ii) consuming second, a salad including fresh uncooked vegetables with 94 wt % water content or more, and fresh uncooked vegetables with 2.8 wt % fiber or more; olive oil; and at least 250 ml of water;
(iii) consuming third, a main meal contemporaneously with consuming the salad, or at least 60 to 90 minutes after consuming the salad;
(iv) consuming fourth, after waiting a minimum of 45 minutes from consuming the salad and/or 60 to 90 minutes after consuming the main meal, a minimum of at least 375 ml of water;
(v) engaging in a physical activity while consuming at least 500 ml of additional water,
wherein the process therapeutically effects in the patient a complete bowel movement, daily bowel movements, increased regular bowel movements, and/or improved stool consistency; and
wherein said therapeutic effects are greater than the effects in a patient not treated thereby and/or, when further threating with a dietary fiber bowel therapy adjuvant, provides said therapeutic effects greater than treating with the dietary fiber bowel therapy alone.

* * * * *